(12) United States Patent
Larson et al.

(10) Patent No.: US 7,144,368 B2
(45) Date of Patent: Dec. 5, 2006

(54) GUIDED RETRACTOR AND METHODS OF USE

(75) Inventors: Jeffrey Larson, Spokane, WA (US); Theodore Bertele, Longmont, CO (US); Louis Greenberg, Boulder, CO (US); Scott Schorer, Niwot, CO (US)

(73) Assignee: Synthes Spine Company, LP, Paoli, PA (US)

(*) Notice: Subject to any disclaimer, the term of this patent is extended or adjusted under 35 U.S.C. 154(b) by 0 days.

(21) Appl. No.: 10/992,260

(22) Filed: Nov. 18, 2004

(65) Prior Publication Data

US 2005/0215862 A1 Sep. 29, 2005

Related U.S. Application Data

(60) Provisional application No. 60/525,732, filed on Nov. 26, 2003.

(51) Int. Cl.
*A61A 1/32* (2006.01)
(52) U.S. Cl. .................... 600/215; 600/222
(58) Field of Classification Search ........... 600/201, 600/215, 219, 222
See application file for complete search history.

(56) References Cited

U.S. PATENT DOCUMENTS

| | | | |
|---|---|---|---|
| 835,968 A * | 11/1906 | Mennes ............... 601/40 |
| 2,670,731 A | 3/1954 | Zoll et al. |
| 3,044,461 A | 7/1962 | Murdock |
| 3,227,156 A | 1/1966 | Gauther |
| 3,749,088 A | 7/1973 | Kohlmann |
| 3,807,393 A | 4/1974 | McDonald |
| 4,765,311 A | 8/1988 | Kulik et al. |
| 4,817,587 A | 4/1989 | Janese |
| 4,913,134 A | 4/1990 | Luque |
| 4,950,270 A | 8/1990 | Bowman et al. |
| 4,984,564 A | 1/1991 | Yuen |
| 5,027,793 A | 7/1991 | Engelhardt et al. |
| 5,052,373 A | 10/1991 | Michelson |
| 5,071,410 A | 12/1991 | Pazell |
| 5,125,396 A | 6/1992 | Ray |
| 5,131,382 A | 7/1992 | Meyer |
| 5,197,971 A | 3/1993 | Bonutti |

(Continued)

FOREIGN PATENT DOCUMENTS

DE 40 28 651 A1 3/1992

(Continued)

OTHER PUBLICATIONS

Thongtrangan et al., "Minimally invasive spinal surgery: a historical perspective," Neurosurg Focus 16 (1): Article 13, 2004.

(Continued)

*Primary Examiner*—Cary E. O'Connor
(74) *Attorney, Agent, or Firm*—Jones Day

(57) ABSTRACT

The present invention provides methods and apparatus in which a surgical retractor comprises a plurality of mechanically coupled tissue retaining walls that are guided into position along one or more guides previously implanted into the patient. The walls are preferably coupled by pivots, so that separating some of the walls from one another opens an operating space. There are preferably two guides, which are driven or screwed into the pedicles of vertebrae, or other bone. Oversized channels are best disposed in a frame, which also serves to hold lock the walls apart. Various convenience features are contemplated including a web disposed between the walls, which expands as the walls are separated. Also contemplated are projections from near the bottoms of one or more of the walls, which can alternatively or additionally help to hold the underlying tissue in place.

9 Claims, 16 Drawing Sheets

U.S. PATENT DOCUMENTS

| | | | |
|---|---|---|---|
| 5,303,694 A | 4/1994 | Mikhail | |
| 5,312,417 A | 5/1994 | Wilk | |
| 5,395,317 A | 3/1995 | Kambin | |
| 5,503,617 A | 4/1996 | Jako | |
| 5,569,300 A * | 10/1996 | Redmon | 606/207 |
| 5,707,390 A | 1/1998 | Bonutti | |
| 5,728,046 A | 3/1998 | Mayer et al. | |
| 5,730,757 A | 3/1998 | Benetti et al. | |
| 5,795,291 A | 8/1998 | Koros et al. | |
| 5,928,139 A | 7/1999 | Koros et al. | |
| 5,944,658 A | 8/1999 | Koros et al. | |
| 5,951,466 A | 9/1999 | Segermark et al. | |
| 5,954,635 A | 9/1999 | Foley et al. | |
| 5,976,146 A | 11/1999 | Ogawa et al. | |
| 6,007,487 A | 12/1999 | Foley et al. | |
| 6,030,340 A | 2/2000 | Maffei et al. | |
| 6,063,088 A | 5/2000 | Winslow | |
| 6,083,154 A | 7/2000 | Liu et al. | |
| 6,090,113 A | 7/2000 | Le Couedic et al. | |
| 6,102,852 A * | 8/2000 | Liu | 600/219 |
| 6,162,172 A | 12/2000 | Cosgrove et al. | |
| 6,187,000 B1 | 2/2001 | Davison et al. | |
| 6,206,826 B1 | 3/2001 | Mathews et al. | |
| 6,235,028 B1 | 5/2001 | Brumfield et al. | |
| 6,354,995 B1 | 3/2002 | Hoftman et al. | |
| 6,394,950 B1 | 5/2002 | Weiss | |
| 6,416,518 B1 | 7/2002 | DeMayo | |
| 6,468,207 B1 | 10/2002 | Fowler, Jr. | |
| 6,471,644 B1 | 10/2002 | Sidor, Jr. | |
| 6,488,620 B1 | 12/2002 | Segermark et al. | |
| 6,520,907 B1 | 2/2003 | Foley et al. | |
| 6,530,926 B1 | 3/2003 | Davison | |
| 6,537,323 B1 | 3/2003 | Weinstein et al. | |
| 6,596,008 B1 | 7/2003 | Kambin | |
| 6,616,605 B1 | 9/2003 | Wright et al. | |
| 6,676,665 B1 | 1/2004 | Foley et al. | |
| 6,746,396 B1 | 6/2004 | Segermark et al. | |
| 6,800,084 B1 | 10/2004 | Davison et al. | |
| 6,811,558 B1 | 11/2004 | Davison et al. | |
| 6,849,064 B1 | 2/2005 | Hamada | |
| 2002/0111538 A1 | 8/2002 | Wright et al. | |
| 2002/0123668 A1 | 9/2002 | Ritland | |
| 2003/0073998 A1 | 4/2003 | Pagliuca et al. | |
| 2003/0139648 A1 | 7/2003 | Foley et al. | |
| 2003/0149341 A1 | 8/2003 | Clifton | |
| 2003/0191371 A1 | 10/2003 | Smith et al. | |
| 2003/0199871 A1 | 10/2003 | Foley et al. | |
| 2003/0236447 A1 | 12/2003 | Ritland | |
| 2004/0002629 A1 | 1/2004 | Branch et al. | |
| 2004/0059193 A1 | 3/2004 | Famous | |
| 2004/0059339 A1 | 3/2004 | Rochm, III et al. | |
| 2004/0138534 A1 | 7/2004 | Ritland | |
| 2004/0181231 A1 | 9/2004 | Emstad et al. | |
| 2004/0186346 A1 | 9/2004 | Smith et al. | |
| 2004/0215199 A1 | 10/2004 | Zinkel | |
| 2004/0236317 A1 | 11/2004 | Davison | |
| 2004/0236331 A1 | 11/2004 | Michelson | |
| 2005/0010293 A1 | 1/2005 | Zucherman et al. | |
| 2005/0070765 A1 | 3/2005 | Abelgany et al. | |
| 2005/0080418 A1 | 4/2005 | Simonson et al. | |
| 2005/0090899 A1 | 4/2005 | DiPoto | |

FOREIGN PATENT DOCUMENTS

| | | |
|---|---|---|
| EP | 0 455 282 | 11/1991 |
| EP | 0 792 620 A2 | 3/1997 |
| EP | 1 192 905 A1 | 4/2002 |
| FR | 2 692 468 | 12/1993 |
| WO | WO 96/02195 | 2/1996 |
| WO | WO 98/12960 | 4/1998 |

OTHER PUBLICATIONS

Muller et al., "A Keyhole Approach for Endoscopically Assisted Pedicle Screw Fixation in Lumbar Spine Instability." Neurosurgery, vol. 47, No. 1, Jul. 2000.

Duncan J. Turner, "A New, Radially Expanding Access System for Laparoscopic Prodedures versus Conventional Cannulas," The Journal of the American Association of Gynecologic Laparoscopists, vol. 3, No. 4, Aug. 1996.

Parviz Kambin, "The Role of Minimally Invasive Surgery in Spinal Disorders," Advances in Operative Orthopedics, vol. 3, pp. 147-171, 1995.

* cited by examiner

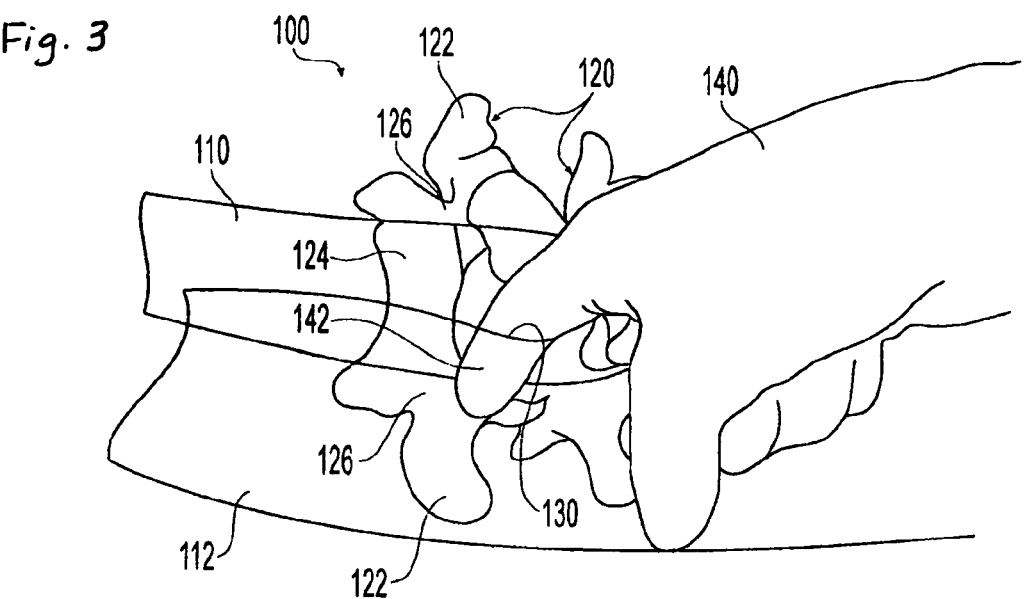
Fig. 3
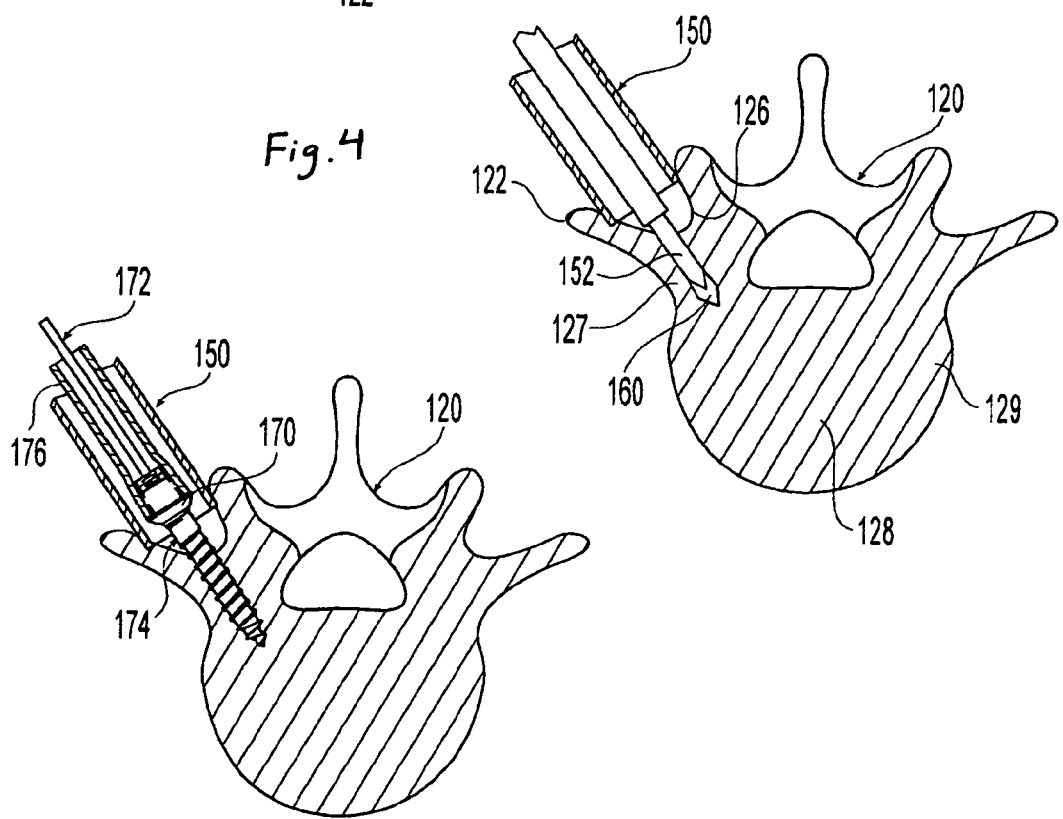
Fig. 4
Fig. 5

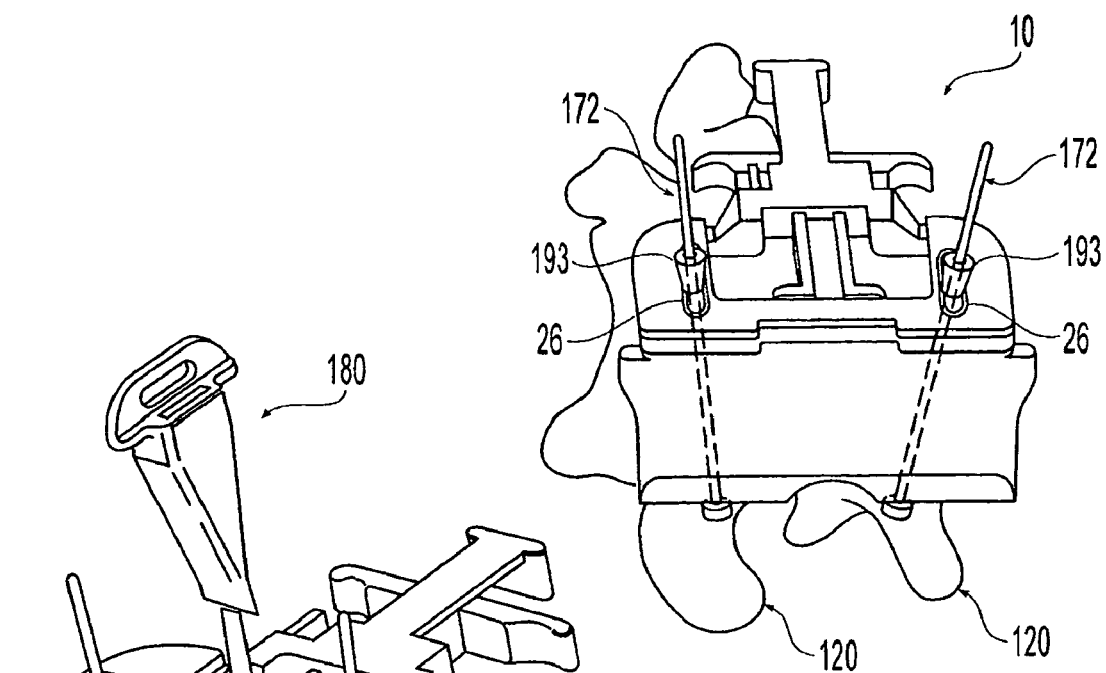
Fig. 6
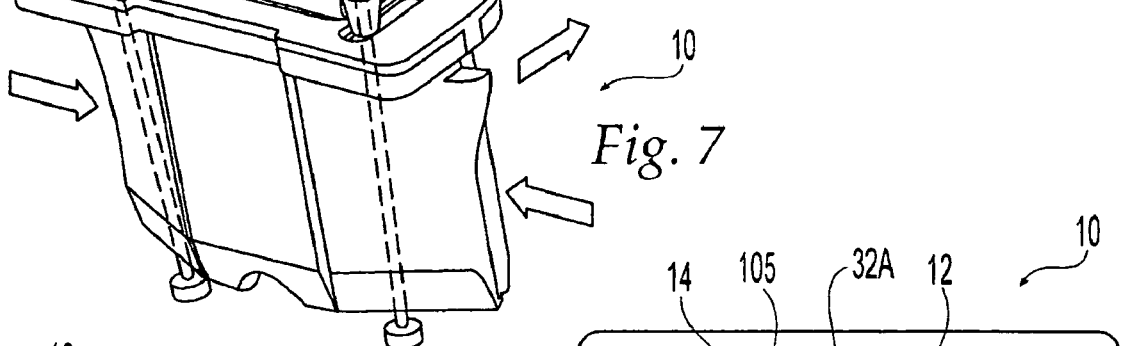
Fig. 7
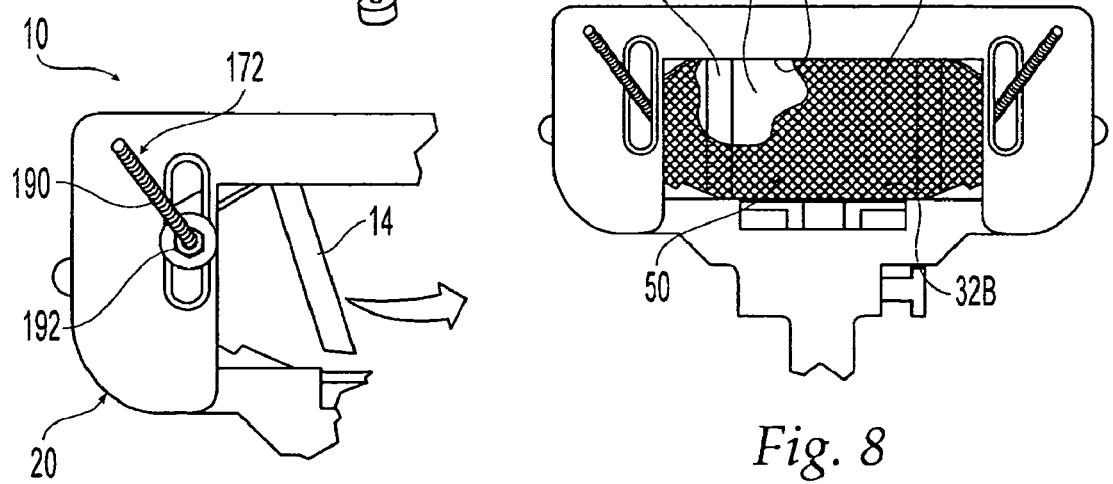
Fig. 8
Fig. 9

GUIDED RETRACTOR AND METHODS OF USE

CROSS-REFERENCE TO RELATED APPLICATIONS

This application is a Continuation application of U.S. Provisional Application Ser. No. 60/525,732, filed Nov. 26, 2003, the contents of which are incorporated by reference herein.

FIELD OF THE INVENTION

The field of the invention is surgical retractors.

BACKGROUND OF THE INVENTION

Many types of surgical retractors are known. The simplest devices are tubular probes, or probes adapted with a paddle or other somewhat flatter surface. Recent embodiments of that concept are depicted in U.S. Pat. No. 6,206,826 to Mathews et al. (March 2001). More complicated retractors utilize scissors, bow string, or screw-jack expanders that operate against mating paddles. Those retractors have the advantage of being able to lock the paddles in place, leaving at least one of the surgeon's hands free for other actions. See e.g., U.S. Pat. No. 6,471,644 to Sidor (October 2002). Still other retractors are self opening, including Cosgrove et al., U.S. Pat. No. 6,162,172 (December 2000). All cited patents herein are incorporated herein by reference.

While undoubtedly useful in many respects, none of the above-mentioned retractors are readily fixed in position relative to one or more bones. U.S. Pat. No. 5,027,793 to Engelhardt et al. (July 1991) addresses that need to some extent, by providing spikes on the bottom of a retractor wall, and further providing spikes that can be driven into the bone. The contemplated use is to resect the operating area down to the bone, position the retractor, and then pound both the retractor and the spikes into place.

A problem remains, however, in that the resection required to properly position the retractor can cause considerable trauma to the overlying and surrounding tissues. Another problem is that multiple retractors are needed to retain tissue pushing into the operating area from different directions. The Engelhardt et al. retractor, for example, did not have to address that issue because the preferred application was acetabular surgery, in which the major encroachment was from gluteus muscles that are all substantially superior to the operating site.

In spinal and some other surgeries these problems can be especially severe. Thus, there is still a need to provide methods and apparatus in which an operating space can be positioned and opened with respect to specific areas of bone, while reducing trauma to surrounding tissue.

SUMMARY OF THE INVENTION

To that end the present invention provides methods and apparatus in which a surgical retractor comprises a plurality of mechanically coupled tissue retaining walls, which are guided into position along one or more guides previously implanted into the patient.

Preferred embodiments utilize two main walls, and four smaller walls, one on each of the ends of the two main walls. In such embodiments all of the walls are coupled by pivots, such that the faces of the two main walls can be moved towards or apart from each other to open or close an operating space. The faces of at least the main walls are preferably flat, but can be any other suitable shape, including convex. The invention is particularly suited for operating on or near curved bony surfaces, and the bottoms of the walls can be compliant (i.e., advantageously adapted to fit and/or conform to the bone surface below).

There are preferably two guides, which are driven or screwed into the pedicles of vertebrae, or other bone. The various guides can be implanted into different bones, or different areas of the same bone. Since practical considerations will usually mean that the guides are parallel to one another, the retractor has oversized channels to receive the guides. The channels can be circular in cross section, but are more preferably elongated into an oblong or other slotted shape.

The channels are best disposed in a frame, which also serves to hold lock the walls apart. Any suitable devices can be used to move apart the main walls to open the operating space, including for example a simple wedge or T-bar, or a mechanism disposed on the frame. The frame can be held in place relative to the guides by wires, nuts, clamps, and so forth.

Various convenience features are contemplated including a web disposed between the walls, which expands as the walls are separated. The web can be cut, torn, bent away, or otherwise manipulated to expose the tissue below. Also contemplated are projections from near the bottoms of one or more of the walls, which can alternatively or additionally help to hold the underlying tissue in place, and can similarly be removed in any suitable manner from the corresponding wall. The frame or other portion of the retractor can be transparent to aid in surgeon visualization.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 3 is a perspective view of the back and spine of a patient, in which finger dissection is being employed to locate a pedicle of a vertebra.

FIG. 4 is a horizontal cross-sectional view of a vertebra, showing use of an awl to punch a guide hole into a pedicle.

FIG. 5 is a horizontal cross-sectional view of the vertebra of FIG. 4, in which a screw is being screwed into the hole created in FIG. 4.

FIG. 6 is a perspective view of the back and spine of a patient in which the closed retractor of FIG. 2 is being fitted onto the guides implanted into adjacent vertebrae.

FIG. 7 is a perspective view of the back and spine of the patient of FIG. 6 in which the retractor is being opened by an opening tool.

FIG. 8 is a perspective view of the back and spine of the patient of FIG. 6 in which the retractor has been opened, and the web is being removed to expose various fingers and the underlying tissue.

FIG. 9 is a perspective view of the back and spine of the patient of FIG. 6 in which the retractor has been opened, and various fingers (bottom tissue retainers) are being removed.

FIG. 30 shows a retractor having angled end walls which facilitate the making of a shorter incision.

DETAILED DESCRIPTION OF THE INVENTION

Figure 1:
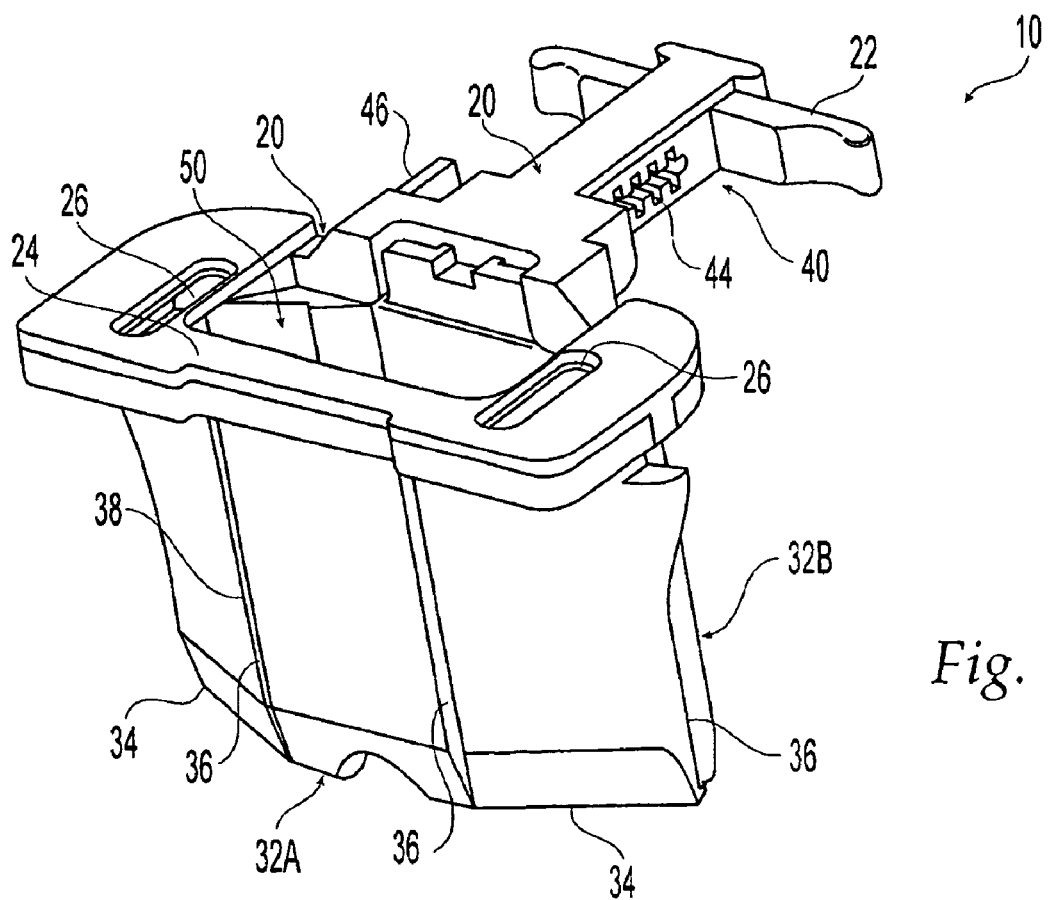
FIG. 1 is a perspective view of a retractor according to the inventive subject matter, in an open configuration.

FIG. 1 generally depicts a retractor 10, having a frame 20, major walls 32A, 32B and minor walls 34, and a locking/opening mechanism 40. The various walls 32A, 32B, 34 are coupled by six hinges 36, and in the open position depicted in the figure cooperate to define an operating space 50.

The frame 20 can be any suitable size and shape according to the particular applications, with larger frames being generally more useful for larger incisions. For posterior lumber surgery on adult humans, the overall dimensions of an especially preferred frame are about 5.5 cm in depth, 3.5 cm in length, 3 cm in width. Frame 20 is preferably made from Delrin®, but can be made of any suitable material, especially a nontoxic polymer such as polyethylene. The frame 20 can advantageously be colored to reduce glare from operating room lighting, and some or all of the frame can be relatively transparent.

Frame 20 generally comprises a handle portion 22 that includes the locking mechanism 40, and a perimeter 24 around the operating space 50. The locking mechanism 40 is shown as a ratchet, but all other suitable locking mechanisms are also contemplated, especially those that provide for a high degree of reliability and ease of operation. At least one of the walls 32A, 32B, 34 is preferably coupled to the perimeter 24 using a pin (not shown).

Channels 26 are located on opposite sides of the perimeter 24, and are each sized to receive one of the guides 172 (see FIGS. 4–9). The system is designed to work with a wide range of pedicle screw or other bone fixation systems, and with various numbers of guides, regardless of the specific relationship between screw and guide. In addition, the passageways defined by the channels 26 should be oversized with respect to the outside diameters of the shafts of the guides 172 so that the channels 26 can receive guides 172 that are out of parallel or in some other manner not perfectly aligned with each other. In preferred embodiments the channels define a passageway having a diameter of about 5 to 15 mm, whereas the guides 172 (see FIGS. 5, 6) preferably have a corresponding diameter of about 4 to 6 mm. All ranges set forth herein should be interpreted as inclusive of the endpoints.

As with other components, the various walls 32A, 32B, 34 are preferably made of a biocompatible material, and here again they can have any suitable sizes and shapes, depending on the surgical site or sites for which they are intended. The currently preferred material for retractor walls is polypropylene. Walls 32A, 32B, 34, for example, can be mostly rectangular in vertical cross-section as shown, with bottoms of at least the major walls 32A, 32B curved to accommodate specific bone shapes, such as that of the spinous processes of the vertebrae in spinal surgery. It is also contemplated that the bottoms of at least the major walls 32A, 32B can be pliable, to conform at least partially to projections and depressions of the underling bone. Walls 32A, 32B, 34 are depicted in the figures as having flat sides, but alternatives can be bowed outwardly (convex), inwardly (concave), or may have any other suitable horizontal cross-section.

One or more of the walls (not shown) can even be inflatable, made out of balloons that define the opening. Of course, the walls 32A, 32B, 34 must be sturdy enough, and therefore thick enough, to withstand the expected forces placed upon them. On the other hand the walls 32A, 32B, 34 are preferably not so thin that they would cut into the tissue below during deployment. On the other hand, the walls 32A, 32B, 34 should not be so thick as to significantly interfere with the size of the operating area. Preferred thickness is from about 3.5 mm to about 5 mm at the thickest point, tapering down to a thickness of 1.5 mm–3 mm at the bottom of each wall. The walls can also be nested in any suitable manner, which simply means that a portion of one wall extends around a portion of another wall.

The hinges 36 are shown as continuations of the walls 32A, 32B, 34. Indeed all of the walls and hinges can be molded as a single piece, with each of the hinges 36 being formed as an especially thin edge of a wall. This is effectively a "living hinge" that can handle multiple openings, using material properties of polypropylene. All other suitable configurations of hinges are also contemplated. For example, instead of four minor walls 34, the major walls 32A, 32B could be coupled by only a single outwardly bowed, flexible piece (not shown) at each end. Certainly the total number of walls can be greater or less than 6.

The term "wall" is used herein in a very broad sense, to mean any sort of tissue retaining barrier, generally longer than tall, and considerably taller than thick. Retractor 10 could thus be termed a "linear retractor" to distinguish it from point retractors that are basically pen-shaped probes. But neither the retractor as a whole nor any of the walls are necessarily linear. The term certainly does not require that the wall be so thin as to constitute a cutting blade. Nor does the term "wall" require that the sides thereof be completely patent. The sides of the walls can be pitted or indented as would occur if the sides had a mesh coating (not shown), and the sides may even have through holes (not shown).

Locking/opening mechanism 40 is shown as a typical ratcheting type mechanism, with teeth 44, and having a release 46. Frame 20 can have both a locking mechanism and an opening mechanism (not shown), or either one by itself. There are numerous other locking and/or opening mechanisms known to the field, and presumably others will become known in the future. It is contemplated that any suitable locking and/or opening mechanisms can be used.

Operating space 50 will be larger or smaller depending on the sizes and shapes of the walls, and the extent to which the walls are separated out from one another. Preferred area of the operating space 50 is between 7 cm$^2$ and 14 cm$^2$.

Figure 2:
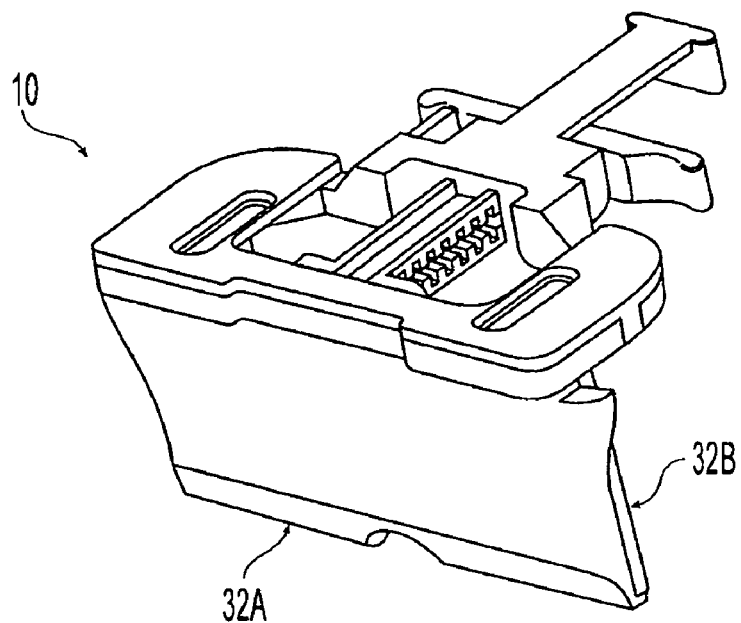
FIG. 2 is a perspective view of the retractor of FIG. 1, disposed in a closed configuration.

FIG. 2 generally depicts the retractor 10 of claim 1, disposed in a closed configuration. The terms "closed" and "open" with respect to configurations of the retractor 10 are relative. Thus, closed merely means substantially closed, but does not require complete closure, so that the walls 32A, 32B are juxtaposed. In a closed position the walls 32A, 32B may well be separated by up to 1 mm or more. Similarly, in a contemplated open configuration, walls 32A, 32B would likely be separated by at least 1.5 cm; but can be separated by up to 2.3 cm or more.

FIG. 3 generally depicts a portion of the spine 100 of a patient, in which the paraspinous muscles are designated schematically by semitransparent bands 110, 112, respectively. The spine 100 includes vertebrae 120, each of which includes transverse processes 122, spinous processes 124, and pedicles 126. An incision 130 has been made, and a finger 142 of hand 140 is being used to dissect through the muscle and locate one of the pedicles 126. Of course a wedge, probe or other tool could be used in place of or in addition to the finger 142 to locate the pedicles.

FIG. 4 generally depicts cannula 150 that positions an awl or probe 152 for use in producing a hole 160 in the pedicle 126. The awl 152 can be manually pushed or otherwise forced through the cortex 127 of the pedicle. Cannula 150 is preferably made of radiolucent material such as plastic or carbon fiber, while awl and probe 152, and other tool attachments and inserts are all preferably made of metal such as surgical steel, titanium, or other durable, radio opaque material. Positioning the cannula 150 can be aided by fluoroscopy or other visualization technique.

In preferred methods, the awl 152 is withdrawn, and a longer, thinner probe (not shown) is inserted through the pedicle 126 into the softer medulla 128 of the body 129 of the vertebra 120. The longer pin is then withdrawn, and in FIG. 5 a screwdriver 176 is used to insert a screw 174. The screw has a head 170, which holds a guide 172 in place. The screwdriver 176 is then removed, leaving the screw 174 implanted into the vertebra 120, and guide 172 rotatably attached to the top of screw 174. The process is repeated to insert another guide 172 into another area of bone, which in the case of spinal surgery is most likely the pedicle of an immediately superior or inferior vertebra on the same side. In other surgeries (not shown), the second, or possibly even a further guide, can be inserted into a different location of the same bone as received the first guide.

In FIG. 6 the guides 172 that are implanted into adjacent vertebrae 120 have been inserted into the channels 26 of the closed retractor 10. Those skilled in the art will realize that the channels can have other configurations besides those shown in the drawing, and can be multi-level rather than simply a single level.

In FIG. 7 the retractor 10 is being opened by an expander 180, which is manually inserted between the opposing walls to produce and widen a gap between them. In this figure the expander generally comprises a wedge with a handle. The expander 180 is preferable over using unassisted fingers because it involves a mechanical advantage. Alternatively, the retractor can be opened using a thumb and fingers-opposing force method using the handle 22 and frame 20. There are numerous alternatives which may or may not involve any mechanical advantage, including for example a T handle coupled to a shaft and a cam (not shown).

In FIG. 8 the retractor 10 has been opened to reveal a web 12 positioned between walls 32A, 32B and 34. The web 12 is preferably a thin, flexible sheet of latex or other biocompatible plastic, which can be easily cut, ripped, or in some other manner disrupted to expose various retaining fingers 14 and the underlying tissue 105. Web 12 is shown as covering the entire floor of the operating space 50, but it could alternatively cover a lesser space, and could extend between or among different walls. The fingers 14 are depicted as extending from or rotating out below the web 12, but some or all of the fingers 14 could alternatively be positioned above the web 12. Each of web 12 and fingers 14 are certainly optional.

In FIG. 9 the retractor 10 has been opened, and various fingers 14 are being removed. Such removal can be accomplished in any suitable manner, including by cutting (as with a scalpel or scissors), bending by hand or with a tool, and so forth. There can be wide fingers, narrow fingers, long or short fingers, closely spaced or widely spaced fingers, flat or rounded fingers, and so on (not shown). Where fingers are used, they are preferably molded as continuous extensions of the walls.

Also shown in FIGS. 8 and 9 are threads 190 the guides 172 can be at least partially threaded, and can thereby that receive wing nuts or other correspondingly threaded pieces 192 that assist in anchoring the frame 20 to the guides 172. In alternative configurations one could use non-threaded lock down pieces such as finger clamps 193. In especially preferred embodiments alternative templates (not shown) can be placed on top of the frame, and held in place using the wing nuts, finger clamps, or other hold-down devices. The frame can also be used to hold additional devices, such as suction or lighting, introduced into the field 50 and held in place by a coupling device on the frame 20.

Although the most preferred embodiments accommodate alignment discrepancies between the guides and the channels with the use of oversized channels, it should be apparent to those of ordinary skill in the art from the disclosure herein that any suitable mechanism can be used to make that accommodation.

Logically, one can modify the guides, the openings or both. The guides can be modified by introducing polyaxial motion at one or more than one location. Thus, contemplated guides could include a ball and socket, hinge, elbow, or other joint at a juncture between the screw portion of the guide and the elongated part of the guide.

Figure 10:
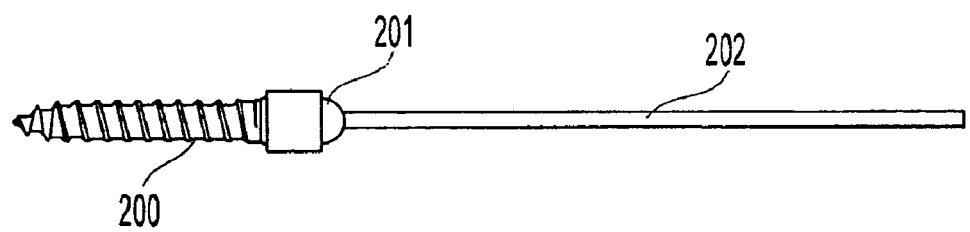
FIG. 10 is a side view of a pedicle screw having a ball and socket joint which facilitates movement of the guide with respect to the pedicle screw, so as to facilitate alignment of the guide with the frame.

FIG. 10 shows a pedicle screw 200 having a ball and socket joint 201 which facilitates movement of the guide with respect thereto, so as to facilitate alignment with the frame.

Additionally or alternatively, contemplated guides can accommodate alignment discrepancies by including a second, third, or other joint higher up (more distally) on the guide. Thus, multiple joints can be utilized to articulate the guides. Any desired combination of types of joints can be used. For example, a first hinge joint which provides for movement of the distal end of a guide in a first direction can be used in combination with a second hinge joint that provides for movement of a distal end of the guide in a perpendicular or other, second direction.

Figure 11:
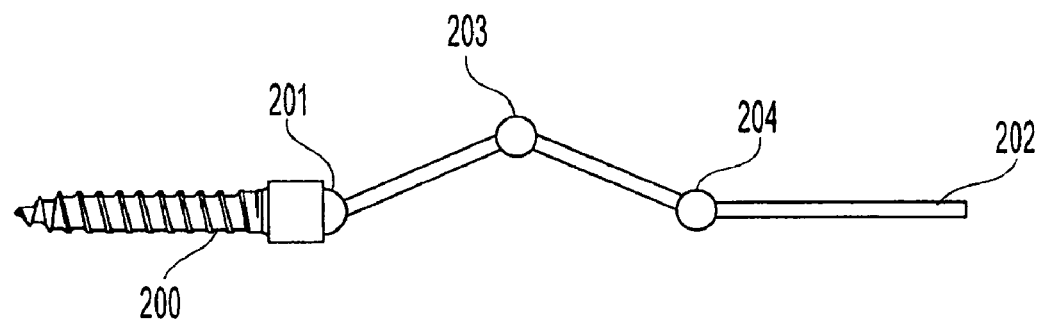
FIG. 11 is a side view of a pedicle screw having a guide attached thereto via first, second and third joints.

FIG. 11 shows a pedicle screw 200 having a guide 202 attached thereto via first 201, second 203 and third 204 joints.

Portions or the entirety the guides could also be made flexible, and thereby introduce polyaxial movement by virtue of bending as opposed to movement at a joint. If only a portion of the guide is made bendable, it is preferred that the bendable portion be relatively close to the screw end because minimal bending movements near the screw (proximal) end are leveraged or exaggerated at the distal end. Certainly, any desired combination of joints and bendable portions of a guide can be utilized to facilitate the required alignment of the guide relative to the guide receiving openings.

Figure 12:
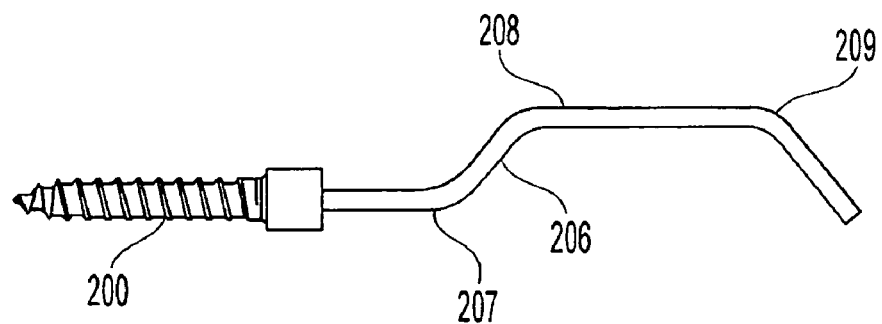
FIG. 12 is a side view of a pedicle screw having a flexible guide attached thereto and showing bends in the flexible guide.

FIG. 12 shows a pedicle screw 200 having a flexible guide 206 attached thereto. The flexible guide has bends 207, 208 and 209 formed therein.

The openings of the retractor can be made to accommodate a degree of misalignment with respect to the guides in any suitable manner. It is especially contemplated that such accommodations can involve an oversized opening, an opening that translates (moves) with respect to a guide or another portion of the frame, and an opening that changes size or shape.

With respect to oversized openings, contemplated opening shapes include circles, ellipses, squares, rectangles, stars, crosses, and indeed any combination of linear and/or curved elements.

Figure 13:
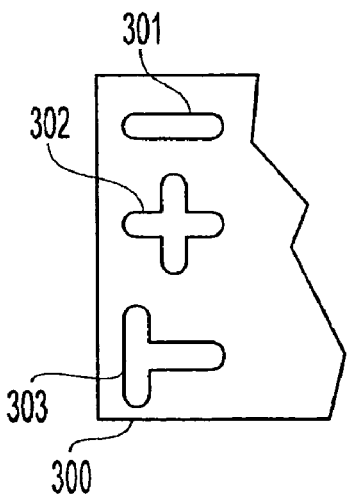
FIG. 13 is a top view of a portion of a retractor frame showing three exemplary oversized openings formed therein.

FIG. 13 shows a portion of a retractor frame 300 having three exemplary oversized openings formed therein. Oversized opening 301 is a slot which can best accommodate misalignment along a single direction (along the longitudinal axis of the slot). Oversized opening 302 is a cross which can best accommodate misalignment along two orthogonal axes (the two longitudinal axes of the two slots which define the cross). Oversized opening 303 is a T which can best accommodate misalignment along two orthogonal axes (the two longitudinal axes of the two slots which define the T).

Openings can be made moveable by including the opening in a portion of the frame that is articulated with respect to the remainder of the frame. For example, an opening that receives a guide can be disposed on a movable arm, or on a portion of the frame that moves with respect to another portion of the frame. The arms or other protrusions can be attached to the retractor via bolts which pass through slots formed in the retractor and/or the arms, such that the position of the arms with respect to the retractor is adjustable. One or more portions of the frame proper can also be bent or otherwise deformed to accommodate alignment of the guides.

Figure 14:
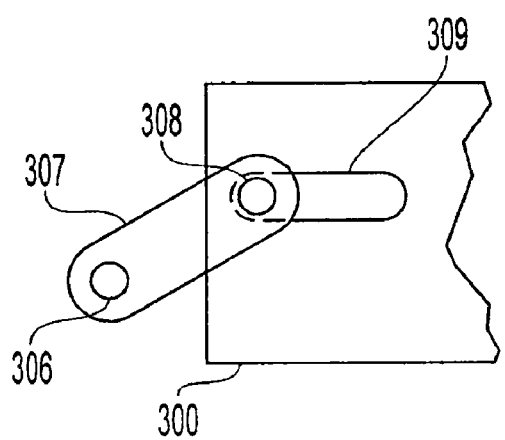
FIG. 14 is a top view of an opening formed in the distal end of an arm which is pivotally and linearly movable with respect to the remainder of the frame.

FIG. 14 shows an opening 306 formed in the distal end of an arm 307 which is movable with respect to the remainder of the frame 300. The arm 307 attaches to the frame 300 via a slot 309 formed in the frame 300. A bolt, rivet, or other fastener (not shown) passes through a hole 308 (or alternatively a slot) in the proximal end of the arm 307. The fastener is both pivotable and slidable within the slot 309 such that the arm 307 can both translate and rotate. The opening 306 may optionally comprise an oversized opening as described above.

Figure 15:
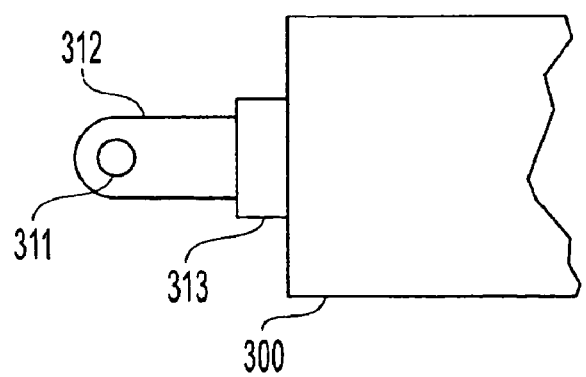
FIG. 15 is a top view of an opening formed in the distal end of an arm which is attached to the frame via an elastomer and is thus movable with respect to the remainder of the frame.

FIG. 15 shows an opening 311 formed in the distal end of an arm 312 which is movable with respect to the remainder of the frame 300. The arm 312 attaches to the frame 300 via resilient elastomer 313, which may be formed of a silicone rubber compound, for example. The elastomer 313 facilitates bending of the arm 312 with respect to the frame 300 and also accommodates some stretching and compression, such that the opening 311 can be translated with respect to the frame (moved in and out with respect thereto). The opening 311 may optionally comprise an oversized opening as described above.

Figure 16:
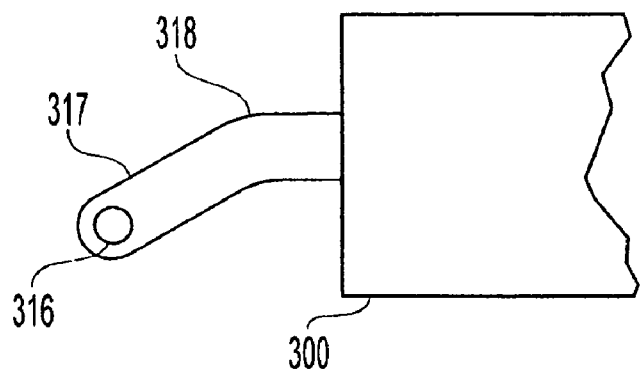
FIG. 16 is a top view of an opening formed in a deformable portion of the frame.

FIG. 16 shows an opening 316 formed upon a deformable portion 317 of the frame 300 which can be bent or otherwise deformed. The deformable portion may, for example, be formed of a bendable metal such as steel or copper. The deformable portion may be covered with a biocompatible sheath or covering, if desired.

Openings can also be "effectively" moved providing an initially large opening, and then constricting the opening by blocking off one or more portions of the opening, or by providing a sliding shuttle within the opening. The opening can also be effectively moved by forming the opening within a material that is subsequently quick cured (perhaps using ultra-violet light) to determine the position of the opening relative to the frame.

Figure 17:
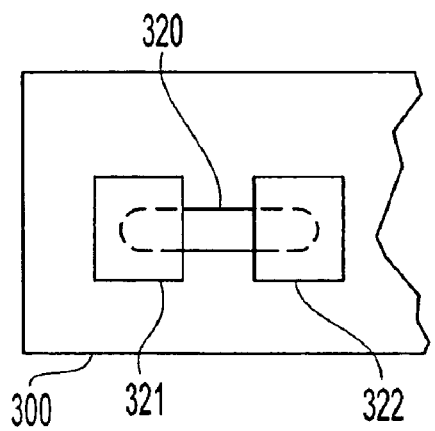
FIG. 17 is a top view of an elongated opening or slot formed in the frame which can be constricted by moving at least one stop.

FIG. 17 shows an elongated opening or slot 320 formed in the frame 300 which can be constricted by moving one or both stops 321 and 322. In this manner, the position of the opening can be move to any desired position along the slot 320. The stops 321 and 322 can be attached to the frame 300 by any desired means, including the use of fasteners and the use of a quick curing adhesive.

Figure 18:
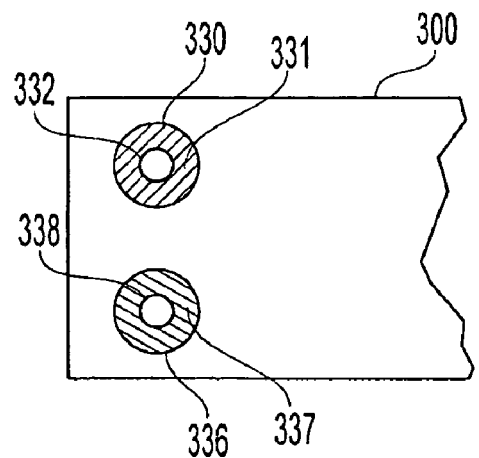
FIG. 18 is a top view of a first opening having an elastomeric material formed therein and generally surrounding a guide and a second opening having a quick cure adhesive formed therein and generally surrounding a guide.

FIG. 18 shows a first opening 330 having an elastomeric material 331 formed therein and generally surrounding a guide 332, such that the elastomeric material 331 accommodates some misalignment of the guide 332 with respect to the frame 300. Optionally, a sleeve or a release agent may be provided intermediate the guide 332 and the elastomeric material 331 to facilitate removal of the retractor.

FIG. 18 also shows a second opening 336 having a quick cure adhesive formed therein and generally surrounding a guide 338, such that the quick cure adhesive accommodates some misalignment of the guide 338 with respect to the frame 300. Optionally, a sleeve or a release agent may be provided intermediate the guide 338 and the elastomeric material 337 to facilitate removal of the retractor.

Figure 19:
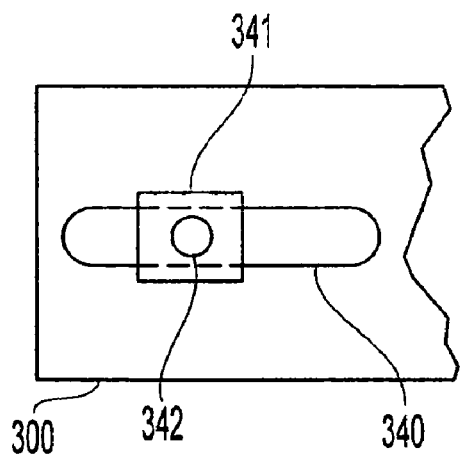
FIG. 19 is a top view of a shuttle which is slidably movable along slot formed in frame.

FIG. 19 shows a shuttle 341 which is slidably movable along slot 340 formed in frame 300. The shuttle has opening 342 formed therein so as to accommodate misalignment along the longitudinal axis of the slot 340. The shuttle can either be a continuous position shuttle, as shown, or a discrete position shuttle. A continuous position shuttle can be positioned at any desired location along the slot 340. By way of contrast, a discrete position shuttle has detents formed along the slot so as to limit placement of the shuttle to discrete, predetermined positions. The opening 342 can optionally be an enlarged opening as described above.

Openings can change size or shape by, among other things, being positioned adjacent an elastomeric material. For example, an opening could be disposed in an elastomeric insert in the frame.

Figure 20:
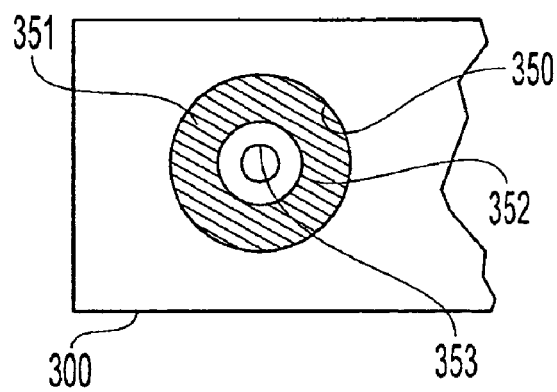
FIG. 20 is a top view of an insert having a opening formed therein, wherein the insert is disposed within an elastomeric material which is formed within a larger opening of the frame.

FIG. 20 shows an insert 352 having an opening 353 formed therein, wherein the insert is disposed within an elastomeric material 351 which is formed within a larger opening 350 of the frame. The opening 353 can optionally be an enlarged opening as described above.

Articulation of the opening can be achieved via the use of a sleeve mounted to the frame, wherein the sleeve slidably receives a rod which as the opening formed upon a distal end thereof.

Figure 21:
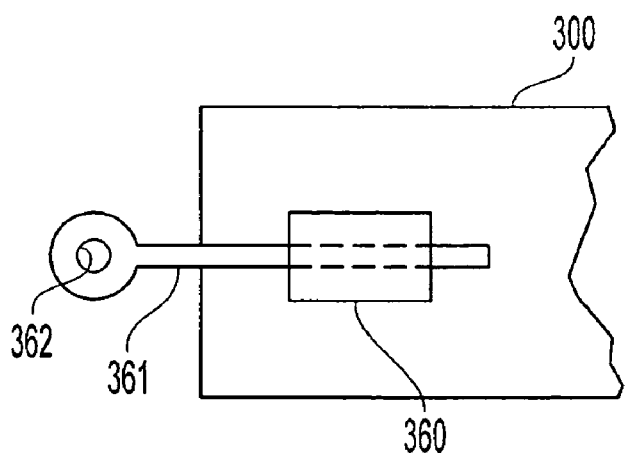
FIG. 21 is a top view of a portion of a frame showing a sleeve formed upon the frame, wherein the sleeve slidably and rotatably receives a rod having an opening formed in a distal end thereof.

FIG. 21 shows a sleeve 360 formed upon the frame 300. The sleeve slidably and rotatably receives rod 361. An opening 362 formed in the distal end of rod 361 receives a guide. The sleeve may be integrally formed with the frame or attached thereto via any desire method. The rod 361 slides into and out of the sleeve to effect translation of the opening 362 and also rotates within the sleeve 360 effect rotation of the opening 362. The opening 362 may be an enlarged opening as described above.

It is important to appreciate that any desired combination of alignment structures and methods can be used upon one or more of the guides and/or guide receiving openings of the retractor. That is, a single guide or guide receiving opening may utilize one or more of these methods and/or two different guides or guide receiving openings may utilize different methods.

Figure 22:
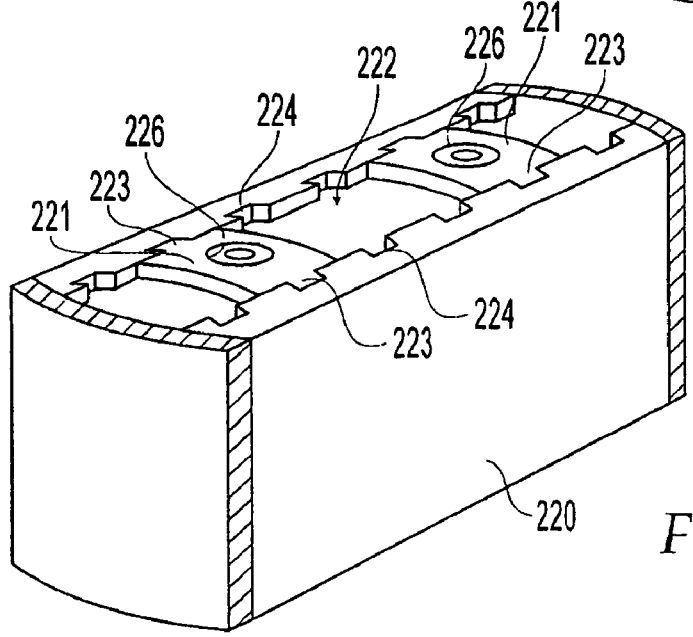
FIG. 22 is a perspective view of an embodiment of a retractor which uses guide inserts to effect expansion thereof.

FIG. 22 shows an embodiment of the retractor 220 which uses guide inserts to effect expansion thereof. The guide inserts 221 are received within central channel 222 at selected ones of a plurality of different predetermined locations. The predetermined locations are defined by locking tabs 223 formed upon the guide inserts 221 which are received by complimentary cutouts 224 formed along the central channel 222.

Figure 23:
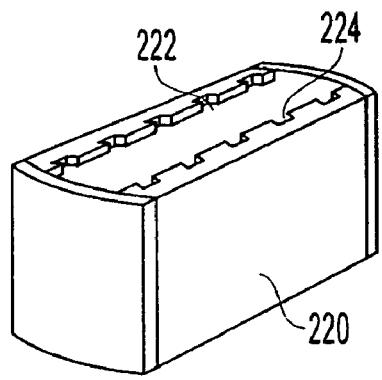
FIG. 23 is a perspective view of the retractor of FIG. 22 in a collapsed configuration.

FIG. 23 shows the retractor of FIG. 22 in a collapsed configuration. The retractor is inserted into an incision in the collapsed configuration and then expended by inserting one or more guide inserts 221 as shown in FIG. 22.

Figure 24:
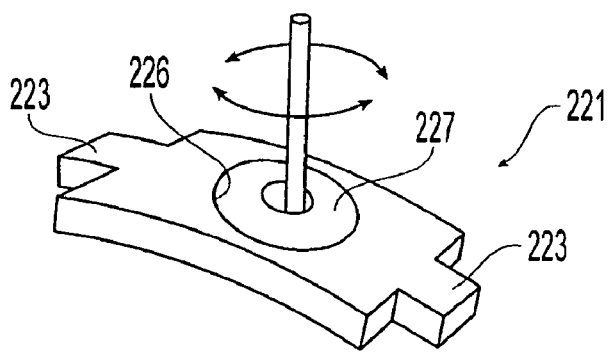
FIG. 24 is an enlarged perspective view of a guide insert.

As best shown in FIG. 24, each guide insert 221 preferably comprises a opening formed therein for receiving a guide. Optionally, an elastomeric material 227 is formed within each opening 226 to accommodate misalignment of the guide as discussed above.

Figure 25:
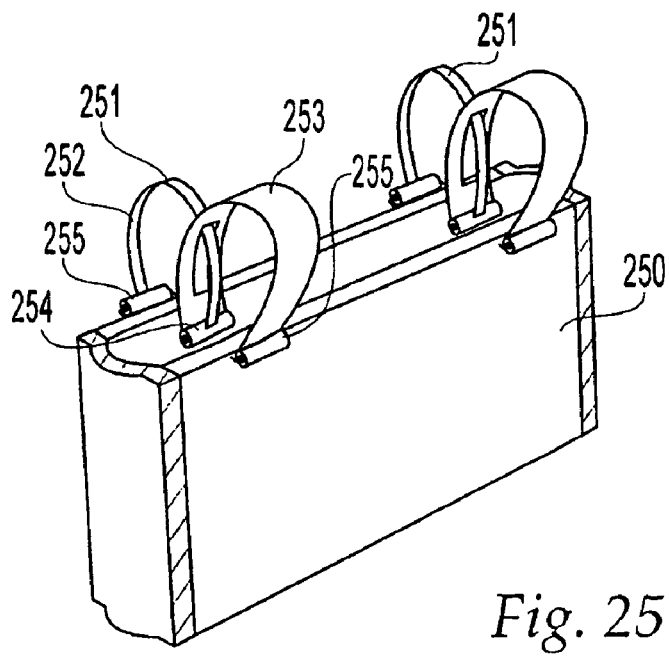
FIG. 25 is a perspective view of an embodiment of the retractor which uses hinged spring clips to effect expansion thereof, showing the retractor in a compressed configuration thereof.

FIG. 25 shows an embodiment of the retractor 250 which uses hinged spring clips 251 to effect expansion thereof. Each hinged spring clip 251 comprises first 252 and second 253 clip members which engage one another via sliding hinge 254 and which are attached to the retractor by hinges 255. Sliding hinge 242 facilitate movement of the first 252 and second 253 clip members between the positions shown in FIGS. 25 and 26 in the same fashion as a similarly configured structure used in climbing protection.

Figure 26:
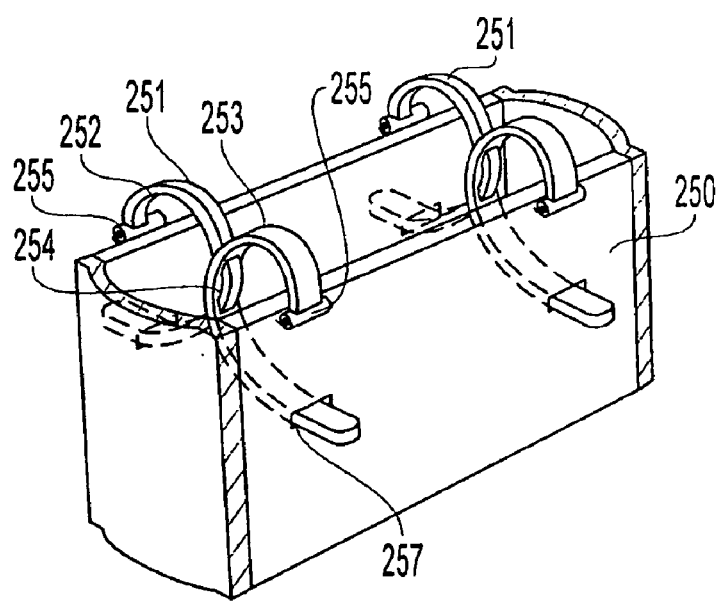
FIG. 26 is a perspective view of the retractor of FIG. 25 in an expanded configuration.

As shown in FIG. 26, the first 252 and second 253 spring clip members cooperate with one another to expand the retractor when pushed downwardly into the retractor. Optionally, the first 252 and the second 253 clip members comprise distal end portions which pass through openings formed in the retractor 250 so as to engage tissue and thus help to stabilize the retractor 250. The distal end portions of the first 252 and second 253 clip members are preferably formed of atraumatic material so as to mitigate tissue damage.

Figure 27:
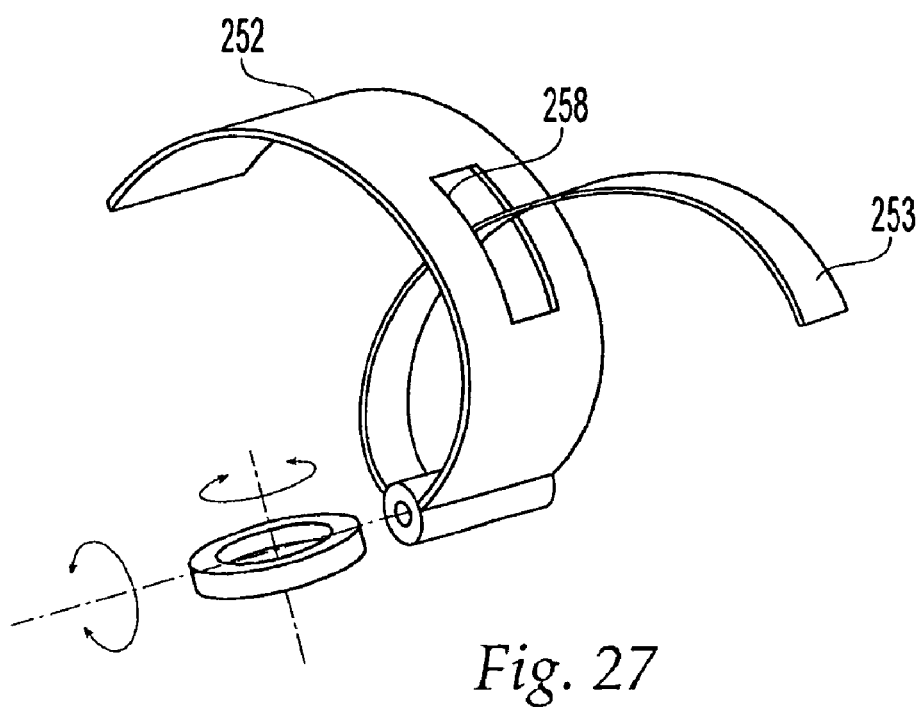
FIG. 27 shows an alternative configuration of the hinge between the first and second spring clip members wherein a sliding and rotating guide hole is attached thereto.

FIG. 27 shows an alternative configuration of the hinge between the first 252 and second 253 spring clip members wherein a sliding and rotating guide hole is attached thereto in a fashion similar to that shown in FIG. 21. Spring clip 253 passes through slot 258 of spring clip 252.

Figure 28:
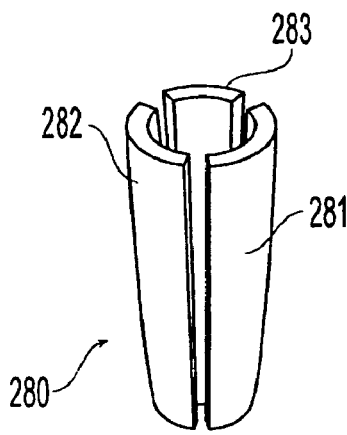
FIGS. 28 and 29 show an open retractor wherein the blades are not (at least initially) attached to one another.
Figure 29:
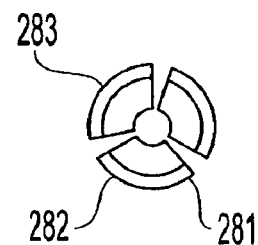

FIGS. 28 and 29 show an open retractor 280 wherein the blades 281, 282, 283 are not (at least initially) attached to one another. Preferably, the blades 281, 282, and 283 become narrower toward the inner end so as to facilitate insertion of the retractor into an incision.

Figure 30:
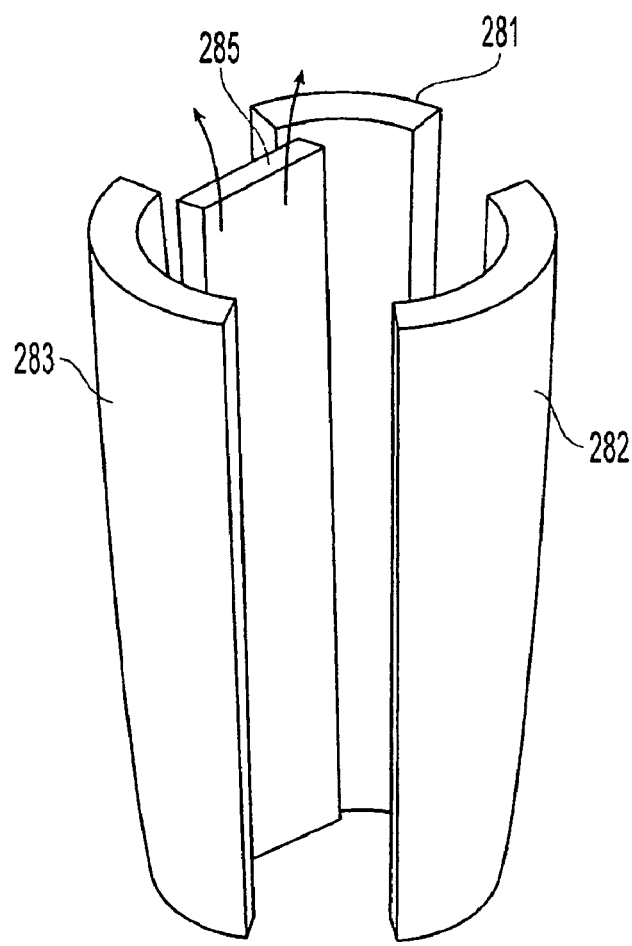
FIG. 30 shows the use one or more spacers inserted between blades to force the blades apart and thus expand the retractor.

As shown in FIG. 30, during use one or more spacers 285 are inserted between the blades 281, 282, 283 to force the blades apart and thus expand the retractor 280. Optionally, the spacer(s) snap to or otherwise engage or fasten to the blades 281, 282, 283 so as to inhibit inadvertent collapse of the retractor 280.

FIG. 30 shows a retractor 300 having angled end walls 302–305 which facilitate the making of a shorter incision. The retractor is shown in FIG. 30 in its collapsed configuration.

Figures 30, 31:
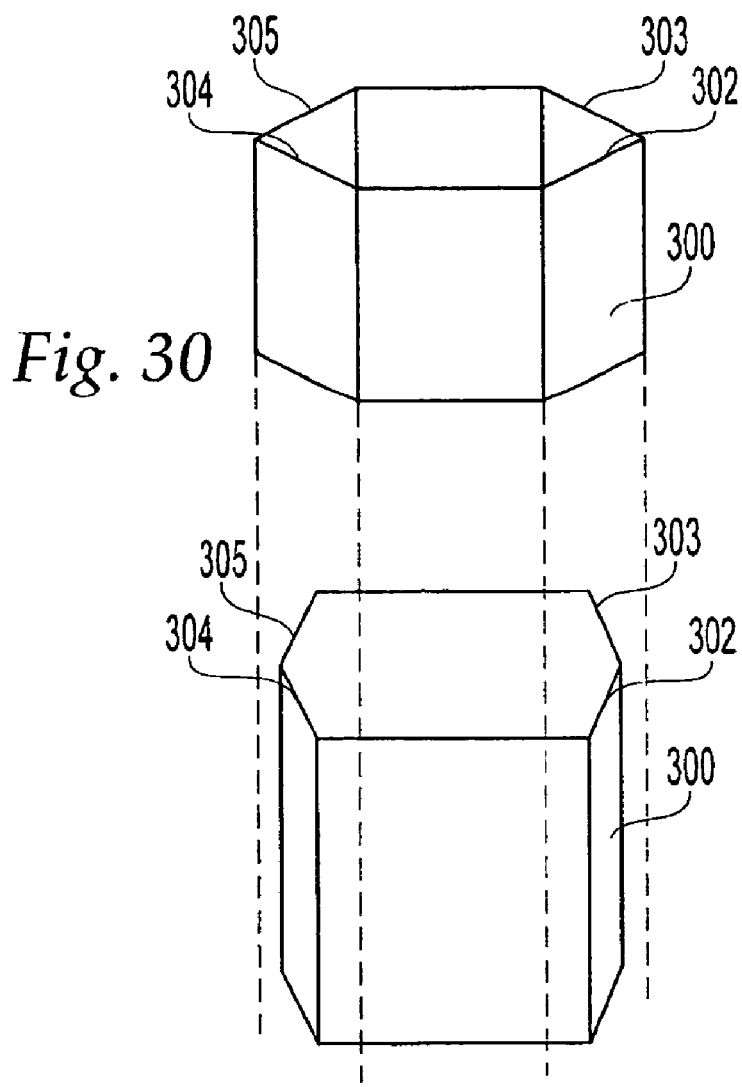
FIG. 31 shows the retractor of FIG. 30 in its expanded configuration.

FIG. 31 shows the retractor 300 of FIG. 30 in its expanded configuration (wherein it is expanded in a transverse direction).

Figure 32:
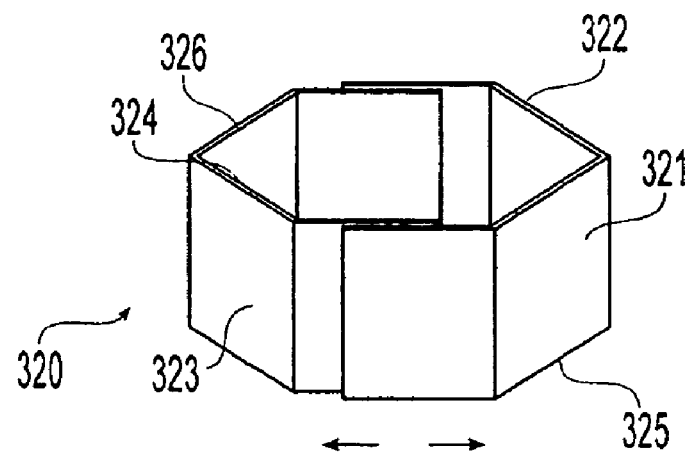
FIG. 32 shows a retractor having angled end wall which facilitate the making of a shorter incision.

FIG. 32 shows a retractor 320 having angled end wall 321–324 which facilitate the making of a shorter incision. The retractor 320 is formed in two sections 325 and 326, which are slidably disposed with respect to one another so as to facilitate retraction along a longitudinal axis thereof.

Figure 33:
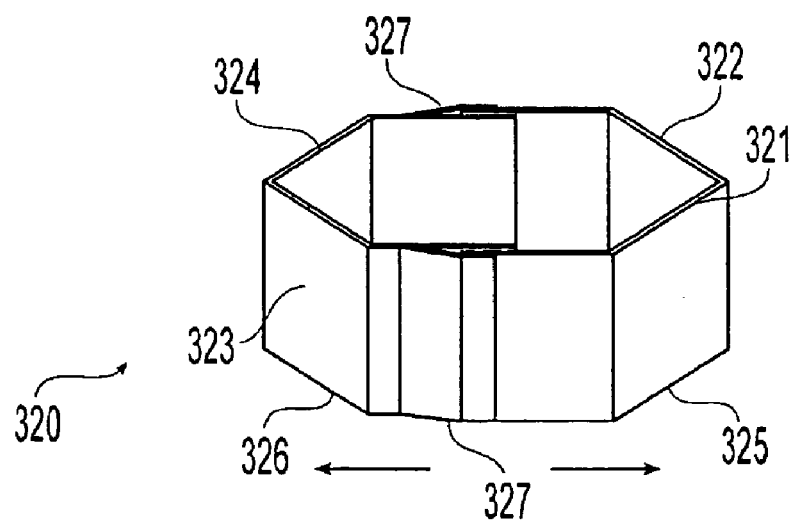
FIG. 33 shows the retractor of FIG. 32 having bellows or elastic members added between the two sections and thereof.

FIG. 33 shows the retractor 320 of FIG. 32 having bellows or elastic members 327 added between the two sections 325 and 326 thereof.

Figure 34:
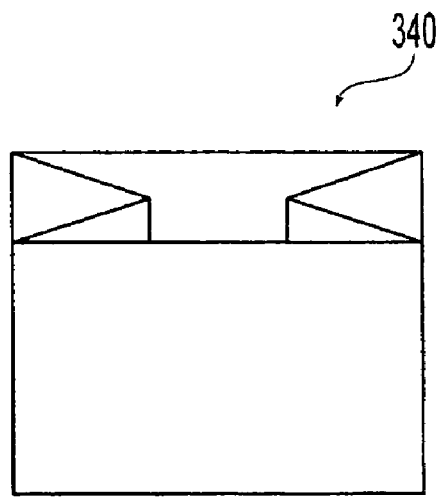
FIG. 34 shows an origami or folded retractor in a compressed configuration thereof.

FIG. 34 shows an origami or folded retractor 340 in a compressed configuration thereof.

Figure 35:
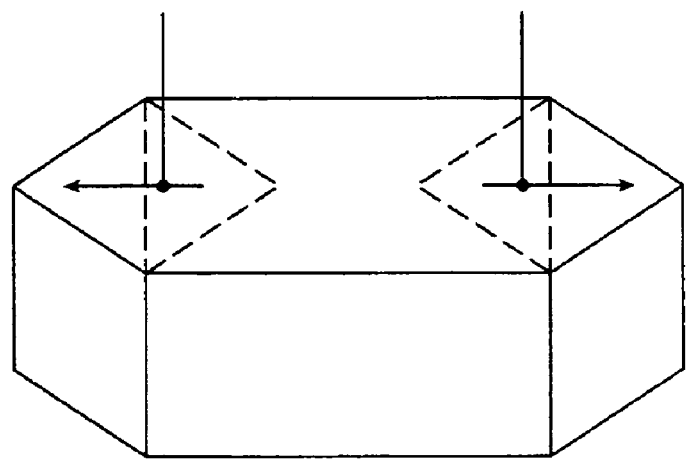
FIG. 35 shows the folded retractor of FIG. 34 in an expanded configuration thereof.

FIG. 35 shows the folded retractor 340 of FIG. 34 in an expanded configuration thereof. It may be necessary for the guides to be located outside of the retractor.

Figure 36:
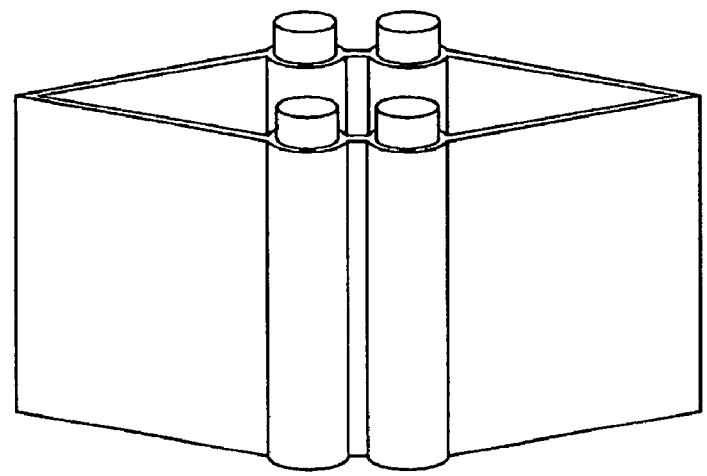
FIG. 36 shows a folded/elastic retractor in a compressed configuration thereof.

FIG. 36 shows a folded/elastic retractor in a compressed configuration thereof.

Figure 37:
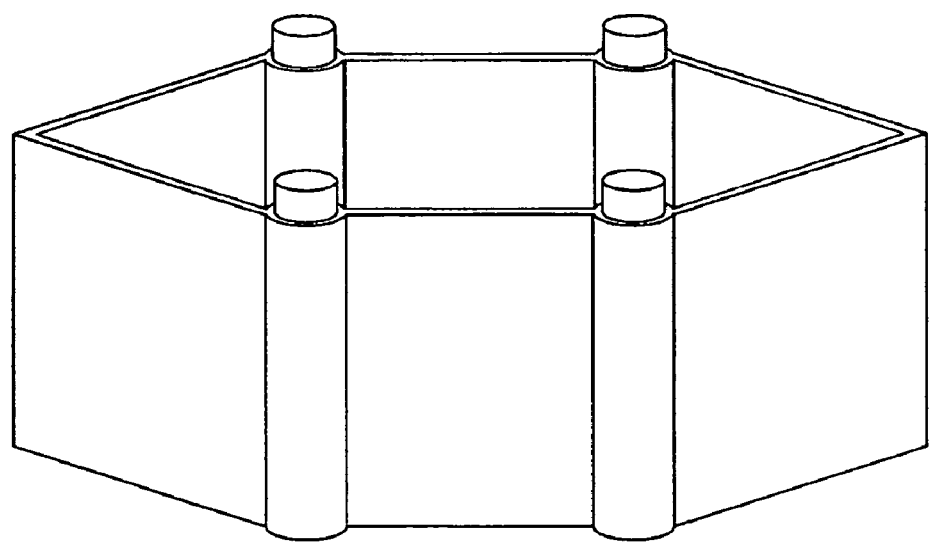
FIG. 37 shows the folded/elastic retractor of FIG. 36 in the expanded configuration thereof.

FIG. 37 shows the folded/elastic retractor of FIG. 36 in the expanded configuration thereof.

Figure 38:
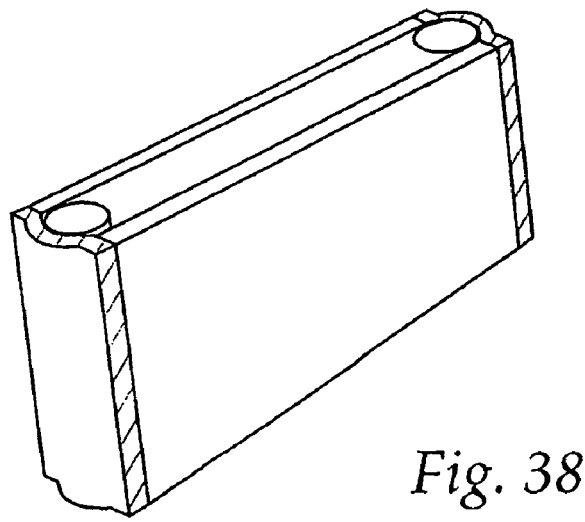
FIG. 38 shows a retractor having rigid sides and elastic end members in a compressed configuration thereof.

FIG. 38 shows a retractor having rigid sides and elastic end members in a compressed configuration thereof.

Figure 39:
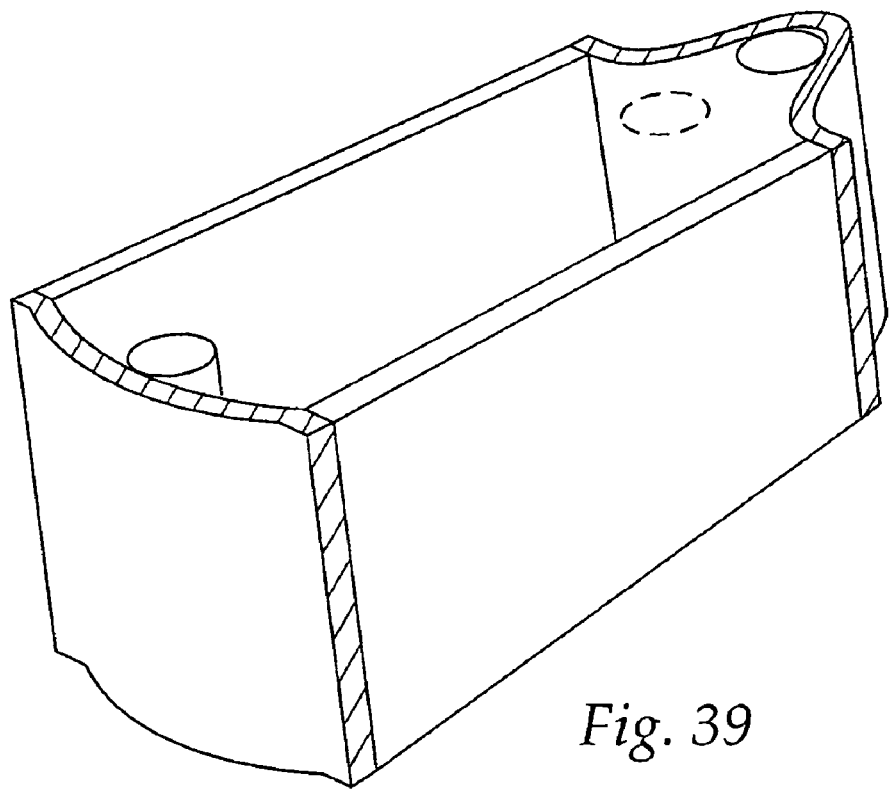
FIG. 39 shows the retractor of FIG. 38 in an expanded configuration thereof.

FIG. 39 shows the retractor of FIG. 38 in an expanded configuration thereof.

Preferred methods of inserting a tissue retractor 10 into a patient involve the steps of providing a retractor 10 having paired tissue retracting surfaces (such as on walls 32A, 32B, 34) and first and second guide receiving areas (such as channels 26); percutaneously or otherwise implanting first and second guides (such as guides 172) into different areas of bone in the patient; then positioning upper ends of the first and second guides through the first and second guide receiving areas, respectively, then fully inserting the retractor down the guides and into the patient, effectively splitting the muscle; and finally moving the tissue retracting surfaces apart from one another to open the operating space. These methods are especially useful where one or more of the guides are screws, which are implanted into very specific anatomical structures such as the pedicles of vertebrae. The contemplated methods are also extremely useful in opening operating spaces overlying adjacent bones. Especially preferred methods optionally employ nuts, clamps, or other readily attachable and tightenable mechanisms to stabilize the retractor 10 on the guides.

From the description above, it should now be apparent that the novel methods and apparatus disclosed herein turn the normal retracting procedure on its head. Instead of positioning the retaining wall or walls and then holding them in place by implanting spikes or posts into the bone, the present procedure implants the spikes or posts, and then uses them as guides to position the retaining wall(s).

The advantages of turning the procedure around are significant. Among other things, this new procedure allows the surgeon to exactly position the retractor 10 at the intended operative site because the positioning can be done precisely with respect to underlying bony structures (e.g., the pedicle 126 of a vertebra). The screws are implanted where the surgeon wants them, and the guides 172, being attached to the top of the screws guide the retractor down into the desired anatomy, splitting the muscles, and defining a operating site 50 within the walls 32A, 32B and 34. After that the operating site 50 is opened, giving the surgeon the desired exposure needed to conduct the surgery, without excess retraction and resulting tissue destruction.

Another advantage is that these new methods and apparatus speed up the procedure and makes more efficient use of resources relative to the prior art. Among other things, after the guides 172 and screws 174 are placed and the retractor 10 is attached and opened, there is no more need for fluoroscopy, which can be moved along to a different room.

Still other advantages involve convenience and reduction in surgeon stress. The novel methods and apparatus make it mentally easier on the surgeon. After the screws 174 are in, in the first part of the procedure, everything else in terms of opening the operating site is fairly straightforward. This helps the surgeon relax mentally and physically.

Thus, specific embodiments and applications of novel retractors have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced.

The invention claimed is:

1. A retractor comprising:
   first and second expandable retractor walls;
   a first spring clip hingedly attached to the first wall, and a second spring clip hingedly attached to the second wall,
   wherein the first and second spring clips are slidably associated; and
   wherein the first and second spring clips provide an expanding force on their respective walls when the spring clips are urged downward.

2. The retractor of claim 1, further comprising a third spring clip hingedly attached to the first wall, and a fourth spring clip hingedly attached to the second wall, wherein the third and fourth spring clips are slidably associated.

3. The retractor of claim 1, wherein the first and second spring clips have a distal end, and wherein the distal end is formed at least partially of an atraumatic material.

4. The retractor of claim 1, wherein the first and second spring clips are slidably associated by way of a sliding hinge.

5. The retractor of claim 4, wherein the sliding hinge is configured to facilitate movement of the first and second spring clips.

6. The retractor of claim 1, wherein the first spring clip passes through at least a portion of the second spring clip.

7. A retractor comprising:
   first and second expandable retractor walls;
   third and fourth retractor walls;
   a first spring clip hingedly attached to the first wall, and a second spring clip hingedly attached to the second wall,
   wherein the first and second spring clips are slidably associated; and
   wherein the first and second spring clips provide an expanding force on their respective walls when the spring clips are urged downward.

8. The retractor of claim 7, wherein the third and fourth retractor walls are comprised of a flexible material.

9. A retractor comprising:
   first and second expandable retractor walls;
   a first spring clip hingedly attached to the first wall, and a second spring clip hingedly attached to the second wall,
   wherein the first and second spring clips are slidably associated;
   wherein the first and second spring clips provide an expanding force on their respective walls when the spring clips are urged downward; and
   wherein the first wall has a slot configured to receive at least a portion of the first spring clip.

* * * * *